United States Patent [19]
Green et al.

[11] 3,932,659
[45] Jan. 13, 1976

[54] BIOLOGICALLY ACTIVE SUBSTANCE

[75] Inventors: Joseph Green, London; Brian Morgan, Reigate, both of England

[73] Assignee: Beecham Group Limited, United Kingdom

[22] Filed: Feb. 25, 1974

[21] Appl. No.: 445,096

Related U.S. Application Data

[63] Continuation of Ser. No. 305,225, Nov. 10, 1972, abandoned, which is a continuation-in-part of Ser. No. 113,052, Feb. 5, 1971, abandoned.

[30] Foreign Application Priority Data

July 24, 1970 United Kingdom............... 35916/70

[52] U.S. Cl. .............................................. 424/325
[51] Int. Cl.² ........................................ A61K 27/00
[58] Field of Search .................................... 424/325

[56] References Cited

UNITED STATES PATENTS

| | | | |
|---|---|---|---|
| 2,979,528 | 4/1961 | Lundsted ........................... | 260/581 |
| 3,579,465 | 5/1971 | Schmolka ........................ | 424/60 X |

*Primary Examiner*—Frederick E. Waddell

[57] ABSTRACT

Certain non-ionic surfactants have been found to be useful in reducing serum cholesterol levels in animals and man. The surfactants are incorporated to at least 20 percent in pharmaceutical compositions so that the ($C_2H_4O$) groups amount to 0 to 30 percent of total molecular weight and the ($C_3H_6O$) groups have a partial molecular weight of 2250 to 3250. The surfactants are prepared by sequential addition of ethylene diamine. "Tetronic 701" and "Tetronic 702" are suitable; others of the same series are not.

4 Claims, No Drawings

BIOLOGICALLY ACTIVE SUBSTANCE

This application is a continuation of application Ser. No. 305,225 filed Nov. 10, 1972 which in turn is a continuation-in-part of application Ser. No. 113,052 filed Feb. 5, 1971, and both now abandoned.

The present invention relates to pharmaceutical compositions for the control and reduction of serum cholesterol levels in animals and man.

Atherosclerosis is a widespread disease in man which is characterised by raised levels of serum lipids, especially by raised serum cholesterol. Clinical opinion at present is that a lowering of serum cholesterol in the adult population is desirable and many efforts have been made, by dietary and therapeutic measures, to achieve this lowering.

There are several ways in which lowering of serum cholesterol can be effected. Thus substances can be given to depress cholesterol biosynthesis or increase the excretion of the products of cholesterol catabolism. However, most of such treatments are not without harmful side-effects. Another way to lower serum cholesterol in animals and man is to inhibit the absorption of cholesterol from the gastro-intestinal tract. Such cholesterol may be either dietary in origin or may be metabolic, arising from the normal biliary flow. We have found a group of compounds which are effective in lowering serum cholesterol, apparently by means of such an effect on gastrointestinal absorption and which are substantially non-toxic at effective dose levels.

It is believed that the mode of action of these compounds is the disruption of the sub-colloidal particles known as micelles.

According to the present invention there is provided a pharmaceutical composition useful for controlling or reducing the serum cholesterol level of an animal or human being comprising at least one non-ionic surfactant of the formula:

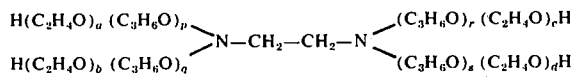

wherein $a$, $b$, $c$, $d$, $p$, $q$, $r$ and $s$ are integers such that the $(C_2H_4O)$ groups account for from 0 to 30 percent of the total molecular weight while the partial molecular weight due to the $(C_3H_6O)$ groups is from 2250 to 3250 together with one or more pharmaceutically acceptable carriers, said surfactant comprising at least 20% by weight of the total composition.

Two or more surfactants of the above formula may be employed in the compositions of this invention.

The surfactants having the above formula are prepared by the sequential addition of ethylene and propylene oxides (randomly) to ethylene diamine.

In forming the novel compositions of this invention, the compound is incorporated in a suitable carrier such as, for example, a pharmaceutical carrier, beverage or foodstuff. The compositions may take the form of tablets, linguets, powders, capsules, slurries, troches or lozenges. Any suitable pharmaceutical carrier may be used for formulating solid compositions such as, for example, magnesium stearate, starch, lactose, glucose, sucrose, rice flour, talc and chalk. The composition may also be in the form of an ingestible capsule (e.g. of gelatin) to contain the compound; or in the form of a syrup, a liquid solution or a suspension. Suitable liquid pharmaceutical carriers include ethyl alcohol, glycerine and saline. Also the compound may be incorporated in a foodstuff such as, for example, in combination with biscuits.

Preferably the compositions of the present invention contain less than 10 percent of water.

The surfactant sold under the trade name Tetronic 701 and manufactured by Wyandotte Chemicals Corporation of Wyandotte, Mich. 48192, U.S.A. is one having the above formula and wherein the $(C_2H_4O)$ groups account for about 10 percent of the total molecular weight and the partial molecular weight due to the $(C_3H_6O)$ groups is about 2750 (i.e. between 2500 and 3000). Consequently this particular surfactant is suitable for use in the present invention.

Similarly, the surfactant sold under the trade name Tetronic 702 and manufactured again by Wyandotte Chemicals Corporation is one having the above formula and wherein the $(C_2H_4O)$ groups account for about 25 percent of the total molecular weight and the partial molecular weight due to the $(C_3H_6O)$ groups is about 2750 (i.e. between 2500 and 3000). Consequently Tetronic 702 is another suitable surfactant.

The compositions of the present invention may be presented in unit dosage form, each unit dosage containing from 10 mg to 1 grm of surfactant e.g. from 100 mg to 500 mg.

In a preferred embodiment, the pharmaceutical compositions of this invention contain the surfactant as the sole pharmacologically active ingredient, preferably in an amount of greater than 75 percent by weight of the total composition.

Also included within the scope of the present invention is a method for controlling or reducing the serum cholesterol levels of an animal or human being, which method comprises the oral administration of one or more non-ionic surfactants defined above. The surfactant or surfactants may be administered alone, in combination with one or more pharmaceutically acceptable carriers, or as part of the total dietary intake. In this latter case, the amount of surfactant employed may be less than 1 percent by weight of the diet and is preferably no more than 0.5 percent by weight. The diet for a man may consist of normal foodstuffs to which the surfactant has been added, and similarly the diet for animals may consist of foodstuffs and the surfactant may be added alone or with a premix. Alternatively it may be added to the drinking water.

In order to achieve an effective degree of serum cholesterol lowering, the surfactant should preferably be administered to the animal or patient in an amount of from 1 to 10 g per day; generally it will be most convenient to spread the daily dosage by giving several smaller, more palatable dosages.

In addition to the serum cholesterol lowering effect of these surfactants, we have noted that some, e.g. Tetronic 701, inhibit to some degree the absorption of fat, thereby reducing the utilisation of fat. Some of the compositions of the present invention therefore appear to have the dual effects of serum cholesterol reduction and reduction in fat utilisation.

The invention will now be further illustrated in the following Examples:

EXAMPLE 1

The hypocholesterolaemic effect of Tetronic 701 and Tetronic 702 was demonstrated in the following experiment:

Male CFY rats (10 per group) weighing 80–100 g were given a hypercholesterolaemic diet containing 63% sucrose, 10% hydrogenated coconut oil, 1% cholesterol and 0.5% ox bile extract, with and without the surfactant at 0.5% in the diet for three weeks. The rats were then killed and their serum analysed for cholesterol.

Table I shows the results of two experiments, and demonstrates the cholesterol lowering effects of Tetronic 701 and 702.

TABLE I

| Expt. | Group | Serum Cholesterol (mg% ± S.E.M.) |
|---|---|---|
| 1 | Control | 245 ± 17 |
|   | Control + Tetronic 701 | 58 ± 3* |
| 2 | Control | 216 ± 26 |
|   | Control + Tetronic 702 | 73 ± 6* |

S.E.M. = Standard Error of Mean.
*Significantly lower than controls (p<0.001)

EXAMPLE 2

The experiments described in Example 1 were repeated using other members of the Tetronic series supplied by Wyandotte Chemicals Corporation. They were random copolymers of ethylene diamine, propylene oxide and ethylene oxides having the same general structural formula of the surfactants useful in this invention, but they did not fulfill the conditions in respect of the relative proportions of $(C_2H_4O)$ groups and $(C_3H_6O)$ groups. The surfactants employed were as follows:

| Surfactant | Approximate Partial molecular weight due to $(C_3H_6O)$ groups. | % of total molecular weight due to $(C_2H_4O)$ groups |
|---|---|---|
| Tetronic 1502 | 6750 | 20% |
| Tetronic 1504 | 6750 | 40% |
| Tetronic 1501 | 6750 | 10% |
| Tetronic 1508 | 6750 | 80% |
| Tetronic 704  | 2750 | 40% |
| Tetronic 1707 | 8750 | 70% |
| Tetronic 304  | 750  | 40% |
| Tetronic 504  | 1750 | 40% |
| Tetronic 1704 | 8750 | 40% |

When the experiments of Example 1 were repeated using these surfactants in place of Tetronic 701 and 702, the results shown in Table II were obtained.

TABLE II

| Expt. | Group | Serum cholesterol (mg% ± S.E.M.) |
|---|---|---|
| 1 | Control | 245 ± 17 |
|   | Control + Tetronic 1502 | 304 ± 17 |
| 2 | Control | 199 ± 19 |
|   | Control + Tetronic 1504 | 228 ± 32 |
| 3 | Control | 199 ± 19 |
|   | Control + Tetronic 1501 | 325 ± 31*** |
| 4 | Control | 199 ± 19 |
|   | Control + Tetronic 1508 | 380 ± 24** |
| 5 | Control | 199 ± 19 |
|   | Control + Tetronic 704 | 185 ± 12 |
| 6 | Control | 216 ± 26 |
|   | Control + Tetronic 1707 | 281 ± 24 |
| 7 | Control | 216 ± 26 |
|   | Control + Tetronic 304 | 287 ± 29 |
| 8 | Control | 216 ± 26 |
|   | Control + Tetronic 504 | 363 ± 30** |
| 9 | Control | 216 ± 26 |
|   | Control + Tetronic 1704 | 233 ± 22 |

**Significantly higher than controls (p.<0.001)
***Significantly higher than control (0.002<p<0.01)

It can be seen that these other members of the Tetronic series of surfactants either raised serum cholesterol levels significantly or caused a statistically insignificant rise (or in the case of Tetronic 704, statistically insignificant fall) in the serum cholesterol levels of the rats.

EXAMPLE 3

In an attempt to discover whether the cholesterol lowering activity of Tetronic 701 and 702 is related to the defoaming properties of the surfactant, Example 1 was repeated substituting two commercial defoaming surfactants for the two Tetronics. The two commercial defoamers were Texafors D4 (a polyoxyethylene ether derivative of a glyceridic oil; Glovers Ltd.) and Antifoam M (a silicone; Midlands Silicones).

The results of repeating Example 1 with these two defoamers are shown in Table III.

TABLE III

| Expt. | Group | Serum cholesterol (mg% ± S.E.M.) |
|---|---|---|
| 1 | Control | 194 ± 27 |
|   | Control + Texafors D4 | 220 ± 27 |
| 2 | Control | 194 ± 27 |
|   | Control + Antifoam M | 196 ± 28 |

It is clear from Table III that the two defoaming agents tested did not lower the serum cholesterol level of the rats.

EXAMPLE 4

Table IV gives the results of the two experiments to examine the effect of Tetronic 701 at a range of dietary concentrations. The rats were given the hypercholesterolaemic diet described in Example 1 and serum cholesterol was measured after three weeks.

In the second of the two experiments, the effect of Tetronic 701 was compared with a recognised hypocholesterolaemic agent Linolexamide (MBLA: α-methylbenzyl-linoleamide). This compound was chosen because its probable mode of action is, like the probable mode of action of Tetronic 701 (and 702) inhibition of gastro-intestinal absorption.

TABLE IV

| Expt. | Group | Serum cholesterol (mg% ± S.E.M.) |
|---|---|---|
| 1 | Control | 293 ± 24 |
|   | Control + 0.25% Tetronic 701 | 71 ± 3* |
|   | Control + 0.10% Tetronic 701 | 85 ± 7* |

TABLE IV-continued

| Expt. | Group | Serum cholesterol (mg% ± S.E.M.) |
|---|---|---|
| 2 | Control | 239 ± 26 |
|   | Control + 0.10% Tetronic 701 | 102 ± 12* |
|   | Control + 0.05% Tetronic 701 | 156 ± 10.7** |
|   | Control + 0.05% MBLA | 222 ± 13 |

*Significantly lower than controls (p <0.001)
**Significantly lower than controls (0.01 <p<0.02).

It appears from Table IV that the hypocholesterolaemic action of Tetronic 701 is apparent even at 0.05 percent of the diet and, at 0.05 percent of the diet, Linolexamide is not as active as Tetronic 701.

EXAMPLE 5

The effect of Tetronic 701 on the utilisation of fat by rats was investigated.

The effect of Tetronic 701 in the diet of rats (a normal rat chow) was estimated by measuring in faecal fat content. The results of these tests are set our in Table V.

TABLE V

|  |  | Growth rate g/rat/day | Faecal fat (% of intake) | Increase over control (% of intake) |
|---|---|---|---|---|
| Control diet |  | 3.3 | 7.7 | 0 |
| Tetronic 701 | 0.1% | 3.3 | 8.6 | 0.9 |
|  | 0.2% | 3.5 | 11.3 | 3.6 |
|  | 0.5% | 2.9 | 21.0 | 13.3 |
|  | 1.0% | 0.6 | 31.0 | 23.3 |

Decreases in fat intake of this order of magnitude have a decided slimming effect due to the high calorific value of fat.

EXAMPLE 6

Soft gelatin coated capsules were each filled with 500 mg of Tetronic 701 or Tetronic 702, and were used for oral administration to humans.

EXAMPLE 7

Tablets were prepared in the usual way each to contain 250 mg Tetronic 701 or Tetronic 702, together with starch, talc, lactose and magnesium stearate, to give tablets weighing 600 mg, again for oral administration to humans.

We claim:

1. A method for reducing the serum cholesterol level of an animal or human being in need thereof, which comprises orally administering to such animal or human being an amount of at least one non-ionic surfactant of the formula:

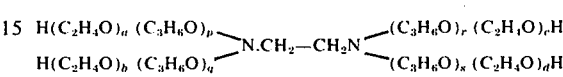

as sole hypocholesterolaemic agent, wherein a,b,c,d,p,q,r and s are integers such that the ($C_2H_4O$) groups account for about 10% of the total molecular weight and the partial molecular weight due to the ($C_3H_6O$) groups is about 2,750.

2. A method for reducing the serum cholesterol level of an animal or human being in need thereof, which comprises orally administering to such animal or human being an amount of at least one non-ionic surfactant of the formula:

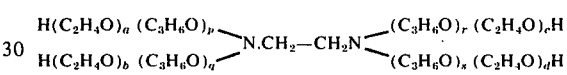

as sole hypocholesterolaemic agent, wherein a,b,c,d,p,q,r and s are integers such that the ($C_2H_4O$) groups account for about 25% of the total molecular weight and the partial molecular weight due to the ($C_3H_6O$) groups is about 2,750.

3. The method of claim 1 wherein the non-ionic surfactant is administered in a composition containing more than 75 percent by weight of the said surfactant combined with a pharmaceutically acceptable carrier.

4. The method of claim 2 wherein the non-ionic surfactant is administered in a composition containing more than 75 percent by weight of the said surfactant combined with a pharmaceutically acceptable carrier.

* * * * *